United States Patent
Hammon et al.

(10) Patent No.: US 7,129,376 B2
(45) Date of Patent: Oct. 31, 2006

(54) METHOD FOR THE PRODUCTION OF A PURIFIED MELT OF AT LEAST ONE MONOMER

(75) Inventors: Ulrich Hammon, Mannheim (DE); Bernd Eck, Viernheim (DE); Dieter Baumann, Walldorf (DE); Joerg Heilek, Bammental (DE); Klaus Joachim Mueller-Engel, Stutensee Blankenlock (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 418 days.

(21) Appl. No.: 10/476,188

(22) PCT Filed: May 2, 2002

(86) PCT No.: PCT/EP02/04793

§ 371 (c)(1),
(2), (4) Date: Nov. 6, 2003

(87) PCT Pub. No.: WO02/090299

PCT Pub. Date: Nov. 14, 2002

(65) Prior Publication Data

US 2004/0147763 A1 Jul. 29, 2004

(30) Foreign Application Priority Data

May 10, 2001 (DE) ............................. 101 22 787

(51) Int. Cl.
*C07C 51/42* (2006.01)
*C07D 207/24* (2006.01)

(52) U.S. Cl. ............... 562/600; 548/543; 548/555
(58) Field of Classification Search ............... 562/600; 548/543, 555
See application file for complete search history.

(56) References Cited

U.S. PATENT DOCUMENTS 5,504,247 A * 4/1996 Saxer et al. ................ 562/600
6,700,016 B1 * 3/2004 Eck et al. ................... 562/600

FOREIGN PATENT DOCUMENTS

| DE | 26 06 364 | 9/1977 |
|----|-----------|--------|
| DE | 199 24 533 | 11/2000 |
| DE | 199 26 062 | 12/2000 |
| DE | 199 38 841 | 2/2001 |
| DE | 100 03 497 | 4/2001 |
| DE | 100 03 498 | 8/2001 |
| DE | 100 26 233 | 11/2001 |
| DE | 100 26 407 | 12/2001 |
| DE | 100 39 025 | 2/2002 |
| DE | 101 15 277 | 6/2002 |
| EP | 0 218 545 | 4/1987 |
| EP | 0 616 998 | 9/1994 |
| EP | 0 847 978 | 6/1998 |
| WO | 94/18166 | 8/1994 |
| WO | 00/45928 | 8/2000 |

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

The invention relates to a method for the production of a purified melt of a monomer melt obtained by condensation, absorption or extraction in a crystallizer, wherein the inlet to the crystallizer is subjected to a mechanical solid/liquid separation operation.

12 Claims, No Drawings

METHOD FOR THE PRODUCTION OF A PURIFIED MELT OF AT LEAST ONE MONOMER

The present invention relates to a process for the preparation of a purified melt of at least one monomer, in which a gas or liquid phase containing the one or more monomers is produced in a first process stage, the one or more monomers are separated from the gas or liquid phase by condensation, absorption or extraction to give a crude melt of the one or more monomers in a first purification stage and the one or more monomers are then separated from the crude melt by crystallization in a second purification stage.

The term monomers in this document is intended to include chemical compounds which have at least one ethylenically unsaturated double bond.

Owing to the one or more ethylenically unsaturated double bonds, monomers form extremely reactive compounds which are used, inter alia, for the preparation of polymers. Typical examples of monomers are acrylic acid, methacrylic acid and N-vinylpyrrolidone.

Usually, monomers are produced by chemical synthesis. However, they are not present directly in pure form but obtained as components of gaseous or liquid mixtures from which they have to be separated. These gaseous or liquid mixtures may be the result of a plurality of successive process steps (including the actual synthesis step), which are to be referred to here together as first process stage. Such a final process step of the first process stage may be, for example, a distillation or rectification in which the monomer is obtained together with impurities accompanying it in the gas phase at the top of the column (or in the upper part of the column) and is separated off by condensation (first purification stage) of said gas phase (cf. for example the isolation of N-vinylpyrrolidone according to DE-A 10026233). However, the final process step of the first process stage may also comprise, as, for example, in the case of the preparation of acrylic acid, direct cooling of the hot gas mixture of a heterogeneously catalyzed gas-phase oxidation with a quench liquid, as described, for example, in DE-A 19924533 and DE-A 10053086. In this case, the acrylic acid is likewise separated from the gas mixture phase by condensation (first purification stage), i.e. by fractional condensation. In an earlier procedure for the preparation of acrylic acid, the acrylic acid is separated from the gas mixture phase by absorption (first purification stage) in a solvent (cf. for example DE-A 10115277).

Often, the monomer of interest is however obtained in the final process step of the first process stage also as a component of a liquid phase from which it is separated by extraction into another liquid (first purification stage).

In all cases described, a liquid which contains the monomers of interest as a main component and should be free of solids is thus obtained without participation of solids, as a result of the first purification stage.

Said liquid is then covered by the term crude melt of the one or more monomers, used in this document, if crystals of the one or more monomers which contain smaller amounts of substances differing from the one or more monomers than the crude melt itself separate out as a first solid on cooling said crude melt.

This means that the term crude melt used here is not applicable when, for example, extracting agent or another component separates out as a first solid on cooling instead of the one or more monomers.

As a rule, those crude melts of the one or more monomers which are important according to the invention contain small amounts of added polymerization inhibitors in solution (cf. for example DE-A 19938841) which are intended to suppress undesired free radical polymerization of the one or more monomers under the action of heat and/or light.

The one or more monomers can be separated by crystallization from the above-defined crude melts of the one or more monomers in a manner known per se by the action of low temperature and a purified melt (in solid or liquid form) of the one or more monomers can thus be prepared (cf. for example DE-A 19926082, WO 00/45928, WO 94/18166, DE-A 10026407, DE-A 10039025, DE-A 10003498 and DE-A 10003497). A very wide range of crystallization processes can be used. In the layer crystallization process, the one or more monomers are frozen out in the form of cohesive, firmly adhering layers.

The solid/liquid separation is effected by simply allowing the residual melt to flow away. The purified crystals can then be melted or can be dissolved in a desired solvent for further use.

In principle, a distinction is made between static and dynamic layer crystallization processes.

In the static process, the crude melt to be purified is introduced, for example, in a tube-bundle heat exchanger or modified plate heat exchanger and then partially solidified by slow temperature reduction on the secondary side. After freezing, the residual melt is discharged and the crystal layer separated off is then melted as purified melt (pure melt), if necessary in stages. The heat and mass transfer to the separation surfaces is effected only by free convection.

Forced convection of the crude melt is typical of the dynamic layer crystallization of crude melts. This can be effected by pumping the crude melt through tubes with plug flow (e.g. German Laid-Open Application DOS 2,606,364), by feeding the crude melt as a falling film (e.g. EP-A 616998) or by passing inert gas into a tube filled with the melt or by pulsation.

In the suspension crystallization process, a crystal suspension which contains the crystals separated off suspended in the residual melt is produced from the crude melt by the action of low temperatures. The solid crystals may be growing directly in suspension or may be deposited as a layer on a cooled wall, from which they are subsequently scraped off and resuspended in the residual melt. The separation of the deposited crystals from the residual melt can be effected in the case of a crystal suspension purely mechanically by pressing, filtration, centrifuging and/or in wash columns.

Typical of all crystallization processes is that they have constrictions, i.e. regions with a narrow flow cross-section for the crude melt, the pure melt and/or the residual melt.

Thus, falling-film crystallizers usually contain, for example, internals which leave only a small flow cross-section. The crude melt passes through this constriction only in the form of a thin film. Behind the constriction, this film is maintained and flows as a falling film down a cooled wall on which crystals are deposited during the flow process (cf. for example EP-B 218545).

The separation of a crystal suspension into crystals and residual melt is almost always effected via cross-sections through which only the residual melt but not the suspended crystals can pass (for example via a two- or three-dimensional network of such cross-sections in the case of filtration or in a screen centrifuge).

Usually, the relevant processes for the preparation of purified melts of at least one monomer by purification of a crude melt by crystallization are carried out more or less continuously (or semicontinuously). A precondition for high space-time yields and long on-stream times is that the narrow flow cross-sections described are not blocked.

When the relevant processes for the preparation of purified melts of at least one monomer is carried out in practice (in particular in the case of acrylic acid, methacrylic acid and N-vinylpyrrolidone), however, such undesired blockages occurred again and again. They did so in particular when a characteristic length of the constrictions was $\leq 5$ mm. It is noteworthy that the material causing the blockage did not consist of crystals since the blockage usually could not be eliminated by heating to above the melting point of the crystals.

It is an object of the present invention to provide a process for the preparation of a purified melt of at least one monomer, in which a gas or liquid phase containing the one or more monomers is produced in a first process stage, the one or more monomers are separated from the gas or liquid phase by condensation, absorption or extraction to give a crude melt of the one or more monomers in a first purification stage and the one or more monomers are then separated from the crude melt by crystallization in a second purification stage, in which process such blockages occur at most to a substantially reduced extent.

We have found that this object is achieved by a process for the preparation of a purified melt of at least one monomer, in which a gas or liquid phase containing the one or more monomer is produced in a first process stage, the one or more monomers are separated from the gas or liquid phase by condensation, absorption or extraction to give a crude melt of the one or more monomers in a first purification stage and the one or more monomers are then separated from the crude melt by crystallization in a second purification stage, wherein the crude melt is subjected to at least one mechanical solid/liquid separation operation on its way out of the first purification stage and into the second purification stage.

The background of the claimed invention is the surprising finding that the crude melts produced in the novel process are not truly free of solids but, in spite of the use of polymerization inhibitors, contain very small amounts of polymer of the one or more monomers to be purified, which polymer is present in disperse (in some cases colloidal) distribution, is formed in an undesired manner and is virtually imperceptible visually and causes the blockage in a purification process carried out continuously (or semicontinuously) over a prolonged period. The described situation where these polymers frequently do not have a particularly high molecular weight and are therefore often tacky is particularly critical.

The novel process is suitable in particular when the melting point of the relevant monomer is $\leq 200°$ C., preferably $\leq 150°$ C., particularly preferably $\leq 100°$ C. or from 5 to 20° C. It is particularly suitable for the preparation of purified melts of acrylic acid, methacrylic acid, alkyl esters of the abovementioned acids and N-vinylpyrrolidone.

In principle, all separation operations which are suitable for separating solids (in particular finely divided ones) from liquids are suitable as a mechanical separation operation to be used according to the invention. Separation operations involving filtration and centrifuging are particularly suitable. Filter materials used may be bar sieves, perforated sieves, woven fabric screens, filter nonwovens, woven filter fabrics, fiber layers, sintered materials or beds (for example of sand).

The pore size of the filter material used is expediently from 50 to 1 000 µm for use in the novel process. Frequently, it should be from 100 to 500 µm. Frequently, however, a range of from 10 to 20 µm or less is also to be used.

The filtration can be effected as a pressure or vacuum filtration. Of course, it may also be carried out by centrifuging using a screen centrifuge. Settling apparatuses (decanters, hydrocyclones, lamellar clarifiers, dwell tanks) are less preferred for the novel process. According to the invention, the filter may also be mounted directly in the outlet of the first purification stage.

The novel process is suitable in particular when the crude melt is subjected to suspension crystallization and the resulting crystal suspension is separated into residual melt and crystals, as described in DE-A 10039025, with the aid of a wash column.

This is true in particular when the relevant monomer is acrylic acid and has been prepared by the route of heterogeneously catalyzed gas-phase oxidation, as described in DE-A 19909923.

EXAMPLES AND COMPARATIVE EXAMPLES

A) 1 t/h of a crude acrylic acid (crude melt) having the following content was produced analogously to example 2 of DE-A 19909923 by fractional condensation of a cooled product gas mixture of a two-stage heterogeneously catalyzed gas-phase oxidation of propene:

| | |
|---|---|
| acrylic acid | 97.3% by weight |
| acetic acid | 0.8% by weight, |
| propionic acid | 500 ppm by weight, |
| furfural | 700 ppm by weight, |
| maleic anhydride | 40 ppm by weight, |
| benzaldehyde | 200 ppm by weight, |
| water | 1.3% by weight and |
| phenothiazine (polymerization inhibitor) | 150 ppm by weight |

The crude melt obtained was transparent and, according to visual inspection, was free of solids. It was fed continuously to a suspension crystallizer. For this purpose, standard chemical pumps of the CPK type (i.e. centrifugal pumps having a double axial face seal), as produced by KSB or Allweiler, were used. The suspension crystallizer was a cooling-disk crystallizer (7 cooling disks, total cooling area about 16 m², the diameter of the circular cooling disks was 1.25 m, 2 500 l internal volume). The feed temperature of the crude melt was 250° C. The heat of crystallization was removed via the cooling surfaces. The residual melt was cooled to 9° C. during passage through the cooling-disk crystallizer. The crystal suspension, which had a solids content of about 25% by weight, was fed continuously from the suspension crystallizer to a two-stage reciprocating-conveyor centrifuge (reciprocating-conveyor centrifuges are described, for example, in the brochure WB210/11.92 AL from Siebtechnik, Mü lheim an der Ruhr, Germany; in a 2-stage reciprocating-conveyor centrifuge, a rotating (larger) outer screen drum (representing the second stage) and a (smaller) rotating inner screen drum (representing the first stage) are arranged concentrically; the outer screen drum executes only rotational movements but no translational movement; the inner screen drum revolves at the same speed as the outer screen drum and is additionally moved back and forth in the axial direction by a hydraulic reciprocating piston; both drums have a screen structure for discharging the liquid; in the feed zone of the inner screen drum, the major part of the residual melt is immediately forced through the screen orifices by centrifugal force; the solid remains behind as a filter cake on the screen; during the axial return movement of the inner drum, an amount of solid corresponding to the translational length is ejected at the free drum end into the outer screen drum and is further dewatered there; during the axial forward movement of the inner screen drum, the filter cake is pushed further stepwise into the outer screen drum (which as a rule is longer than the inner screen drum) and is finally ejected into a collecting channel) on which the suspension crystals were separated from the residual melt. The internal diameter of the first stage was 200 mm. The screen gap width of the first stage was 250 µm. The second stage was conical (the internal diameter widened from 250 mm to 310 mm and the screen gap width was 300 µm). The speed was 2 200 revolutions per minute. The number of strokes of the inner screen drum was 70 per minute.

After the ejected crystals had been melted in a container, a purified acrylic acid melt whose acrylic acid content was >99% by weight was obtained.

After continuous operation of the centrifuge for about three weeks, overshooting of the suspension occurred in the first stage, i.e. the liquid phase was no longer sufficiently separated off in the first stage and flowed in a channel-like manner, via the filter cake formed in the first stage, into the second stage. This is disadvantageous in that it results in an increase in the residual moisture of the crystals ejected from the second stage (from about 7% by weight to >10% by weight) and irregular running of the centrifuge (due to the imbalance caused by the channel formation and filter cake deformation in the first stage), forcing a reduction in speed.

After the installation of two interchangeable filters (stainless steel wire basket filters each having a screen area of 550 cm$^2$ and a screen size of 150 µm) in the feed of the fractional condensation to the suspension crystallizer, no overshooting of the suspension in the first stage was found under otherwise identical operating conditions, even after an operating time of more than four months. When the interchangeable filters were changed, which was carried out about once a week, they were found to contain polyacrylic acid as a rubber-like polymer. This could be washed out with aqueous sodium hydroxide solution and subsequently pure water on the interchangeable filter.

B) An acrylic acid (crude melt) which had a purity of 99.5% by weight (acrylic acid content) and contained 200 ppm by weight of added monomethyl ether of hydroquinone as a polymerization inhibitor was produced analogously to example 1 of DE-A 0.3641996 as a distillation top product of an industrial acrylic acid and was fed to a one-tube falling-film layer crystallization unit (the length of the crystallization tube was 6 m, the internal diameter was 70 mm, the tube material was V2A stainless steel and a mixture of 50% by weight of water and 50% by weight of ethylene glycol at from −20 to +35° C. was used as an external thermostating medium; otherwise, the procedure was as in EP-A 616998; the melting was effected at a layer thickness of 6 to 12 mm) for further purification by crystallization, with a feed temperature of 25° C. The feed was effected by means of standard chemical pumps of the CPK type (i.e. centrifugal pumps having a double axial face seal), as produced by KSB or Allweiler. The crude melt thus fed in was transparent and, on the basis of visual inspection, free of solids. At the upper end, the crystallization tube had a feed collar with orifices having a longest dimension of about 3 mm, via which the crystallization tube was loaded with the crude melt in the form of a falling film. Partial blockage of the feed collar occurred after operation for two weeks.

After installation of a wire basket filter (filter area, about 100 cm$^2$, 500 µm screen size) in the feed to the crystallization tube, no more problems occurred under otherwise identical conditions in the course of 8 weeks of operation. When the wire basket filter was changed, it was found to contain polyacrylic acid as a rubber-like polymer. This could be washed out with aqueous sodium hydroxide solution and subsequently pure water from the interchangeable filter.

We claim:

1. A process for the preparation of a purified melt of at least one monomer, comprising:
    producing a gas or liquid phase containing the at least one monomer in a first process stage,
    separating the at least one monomer from the gas or liquid phase by condensation, absorption or extraction to give a crude melt of the at least one monomer in a first purification stage, and
    separating the at least one monomer from the crude melt by crystallization in a second purification stage,
    wherein the crude melt is subjected to at least one mechanical solid/liquid separation operation on its way out of the first purification stage and into the second purification stage; and wherein the at least one monomer is selected from the group consisting of acrylic acid, methacrylic acid and N-vinylpyrrolidone.

2. The process as claimed in claim 1, wherein the second purification stage is carried out in a falling-film crystallizer.

3. The process as claimed in claim 1, wherein the second purification stage is carried out in a suspension crystallizer.

4. The process as claimed in claim 1, wherein the at least one monomer has a melting point $\leq 200°$ C.

5. The process as claimed in claim 1, wherein the at least one monomer has a melting point $\leq 150°$ C.

6. The process as claimed in claim 1, wherein the at least one monomer has a melting point $\leq 100°$ C.

7. The process as claimed in claim 1, wherein the at least one monomer has a melting point of from 5 to 20° C.

8. The process as claimed in claim 1, comprising:
    subjecting said crude melt to suspension crystallization, thereby obtaining a crystal suspension, and
    separating said crystal suspension into residual melt and crystals.

9. The process as claimed in claim 8, wherein a wash column is used for said separating of said crystal suspension.

10. The process as claimed in claim 8, wherein said separating of said crystal suspension is effected via cross-sections through which the residual melt but not the suspended crystals can pass.

11. The process as claimed in claim 8, wherein said cross-sections have a length of the constriction of $\leq 5$ mm.

12. The process as claimed in claim 8, wherein said cross-sections are not blocked during the process.

* * * * *